United States Patent [19]

Fischer et al.

[11] Patent Number: 4,467,120

[45] Date of Patent: Aug. 21, 1984

[54] PREPARATION OF α,β-UNSATURATED ALDEHYDES AND 2,7-DIMETHYL-OCTA-2,6-DIENAL

[75] Inventors: Rolf Fischer, Heidelberg; Hans-Martin Weitz, Bad Durkheim, both of Fed. Rep. of Germany

[73] Assignee: BASF Aktiengesellschaft, Ludwigshafen, Fed. Rep. of Germany

[21] Appl. No.: 481,836

[22] Filed: Apr. 4, 1983

Related U.S. Application Data

[62] Division of Ser. No. 372,481, Apr. 28, 1982, abandoned.

[30] Foreign Application Priority Data

May 11, 1981 [DE] Fed. Rep. of Germany ....... 3118656

[51] Int. Cl.$^3$ .................... C07C 45/00; C07C 47/20
[52] U.S. Cl. ................... 568/484; 568/485; 568/486; 568/491; 568/496
[58] Field of Search ............ 568/484, 485, 486, 491, 568/496

[56] References Cited

U.S. PATENT DOCUMENTS

| | | | |
|---|---|---|---|
| 2,246,049 | 6/1941 | Lange | 568/484 |
| 3,639,472 | 2/1972 | Sennewald et al. | 568/484 |
| 3,819,715 | 6/1974 | Vogt et al. | 568/484 |
| 3,928,459 | 12/1975 | Mercier | 568/486 |
| 4,239,706 | 12/1980 | Fischer et al. | 568/484 |

FOREIGN PATENT DOCUMENTS

| | | | |
|---|---|---|---|
| 2217452 | 2/1972 | Fed. Rep. of Germany | 568/484 |
| 2417558 | 11/1974 | Fed. Rep. of Germany | 568/484 |
| 2815539 | 10/1979 | Fed. Rep. of Germany | 568/484 |
| 2820519 | 11/1979 | Fed. Rep. of Germany | 568/484 |
| 2927090 | 1/1980 | Fed. Rep. of Germany | . |
| 2847069 | 5/1980 | Fed. Rep. of Germany | 568/484 |
| 2937287 | 5/1980 | Fed. Rep. of Germany | . |

OTHER PUBLICATIONS

Bull. Soc. Chim. France, 11, (1944), 218–223.
Methoden der Organischen Chemie, vol. 6/3, 592–594.
M. A. Valette, Comptes Rendus 223, (1946), 907.
Ch. Prevost, Bull. Soc. Chim. France 11, (1944), 218.
Houben–Weyl, Methoden der Organischen Chemie, vol. I/1, 528, Table 3.
Ullmanns Encyklopädie der Technischen Chemie, 4th revised edition, 7, 118.

*Primary Examiner*—Werren B. Lone
*Attorney, Agent, or Firm*—John H. Shurtleff

[57] ABSTRACT

A process for the preparation of α,β-unsaturated aldehydes by reacting a 1,4-diacyloxyalk-2-ene, which is substituted in the 2-position by an aliphatic radical, with water in the presence of an acid, and of 2,7-dimethylocta-2,6-dienal.

9 Claims, No Drawings

PREPARATION OF α,β-UNSATURATED ALDEHYDES AND 2,7-DIMETHYL-OCTA-2,6-DIENAL

This application is a division of application Ser. No. 372,481, filed Apr. 28, 1982 now abandoned.

The present invention relates to a process for the preparation of α,β-unsaturated aldehydes by reacting a 1,4-diacyloxyalk-2-ene, which is substituted in the 2-position by an aliphatic radical, with water in the presence of an acid, and of 2,7-dimethylocta-2,6-dienal.

It has been disclosed in Bull. Soc. Chim. France 11 (1944), 218–223, that a mixture of aldehydes is obtained when an unsaturated diol is reacted with dilute sulfuric acid or equimolar amounts of phosphoric acid and water. Thus, a mixture of pent-2-enal and pent-3-enal is obtained from pent-2-ene-1,4-diol, a mixture of hex-2-enal and hex-3-enal is obtained from hex-2-ene-1,4-diol, and a mixture of 2,3-dimethylbut-2-enal and 2,3-dimethylbut-3-enal is obtained from 2,3-dimethylbut-2-ene-1,4-diol.

German Published Application DAS No. 2,815,539 and DAS No. 2,847,069 disclose that 2-alkylcrotonaldehydes are obtained when a 2-alkylbut-2-ene-1,4-diol diacylate is reacted with water in the presence of a cation exchanger or of a mineral acid.

We have found that α,β-unsaturated aldehydes of the formula

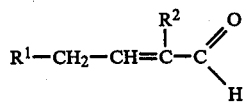

where $R^1$ and $R^2$ are aliphatic hydrocarbon radicals of 1 to 15 carbon atoms are advantageously obtained when a 1,4-diacyloxyalk-2-ene of the formula

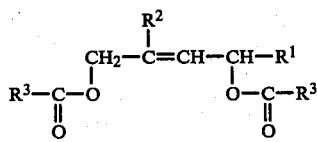

where $R^1$ and $R^2$ have the above meanings and $R^3$ is hydrogen, alkyl, cycloalkyl or aryl, is reacted with water in the presence of a mineral acid or of a cation exchanger.

Where 2,7-dimethylocta-2,6-dienal is prepared from 2,7-dimethyl-1,4-diacetoxyocta-2,7-diene, the reaction can be represented by the following equation:

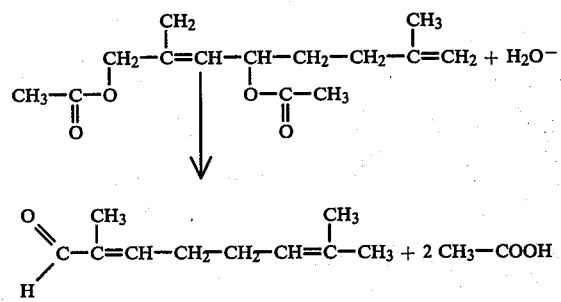

The process according to the invention gives α,β-unsaturated aldehydes by a simple and economical route, and does not require reactants which are expensive or difficult to obtain. The working up procedure is simple. Advantageously, the process can be carried out on an industrial scale. The starting materials can be converted into the α,β-unsaturated aldehyde in a one-stage reaction, without prior conversion to the diol. Large amounts of salt resulting from neutralization are avoided.

On the basis of the prior art given below, it was not possible to predict the mode of reaction, in the presence of water and of a mineral acid or cation exchanger, of a 1,4-diacyloxybut-2-ene of the formula II, which is substituted in the 2-position and 4-position by aliphatic radicals, and/or of the diol formed by hydrolyzing this compound.

According to Houben-Weyl, Methoden der Organischen Chemie, volume 6/3, pages 592 to 594, dihydrofurans are obtained from 1,4-dihydroxybut-2-ene in the presence of acidic catalysts. German Published Application DAS No. 2,062,950 discloses that cis-but-2-ene-1,4-diol monoacetate or diacetate is converted into 2,5-dihydrofuran in the presence of an acid. On the other hand, when cis-1,4-dihydroxybut-2-ene is treated with aqueous sulfuric acid, crotonaldehyde (65%) and 2,5-dihydrofuran (35%) are obtained, while trans-1,4-dihydroxybut-2-ene is converted into crotonaldehyde in quantitative yield (M. A. Valette, Comptes Rendus 223 (1946), 907).

While 2-methylbut-2-enal (tiglic aldehyde) is obtained in yields of up to 98% when 2-methyl-1,4-diacetoxybut-2-ene is reacted with water in the presence of a cation exchanger (German Published Application DAS No. 2,815,539) or of a mineral acid (German Published Application DAS No. 2,847,069), pent-2-enal is obtained in a yield of only 29% when 1,4-diacetoxypent-2-ene is reacted with water in the presence of a cation exchanger (cf. Comparative Example 1). When 1,4-dihydroxypent-2-ene is reacted with from 1 to 25% strength sulfuric acid or with equimolar amounts of phosphoric acid and water, a mixture of pent-2-enal and pent-3-enal is obtained. In the corresponding reaction of 1,4-dihydroxyhex-2-ene, a mixture of hex-2-enal and hex-3-enal is obtained (Ch. Prévost, Bull. Soc. Chim. France 11 (1944) 218). In contrast, 2,5-dihydroxyhex-3-ene can be converted into 2,5-dimethyl-2,5-dihydrofuran, using hydrogen chloride (Houben-Weyl, loc. cit.). In contrast to 2-methyl-1,4-diacetoxybut-2-ene, 2,3-dimethyl-1,4-diacetoxybut-2-ene can be converted into 2,3-dimethylbut-2-enal with a yield of only about 17%, using water in the presence of a cation exchanger (see Comparative Example 2). On the other hand, cis- and trans-2,3-dimethyl-1,4-dihydroxybut-2-ene give mixtures of 2,3-dimethylbut-2-enal and 2,3-dimethylbut-3-enal in the presence of mineral acids (Ch. Prévost, loc. cit.).

In formula II, $R^1$ and $R^2$ are aliphatic hydrocarbon radicals, such as straight-chain or branched alkyl, alkenyl or alkadienyl of 1 to 15, preferably 1 to 10, carbon atoms.

Examples of such radicals are $CH_3$, $C_2H_5$, n—$C_4H_9$, sec.-butyl, —$CH_2$—$C(CH_3)$=$CH_2$, —$CH_2$—$CH$=$CH_2$, —$(CH_2)_2$—$C(CH_3)$=$CH_2$, —$CH_2$—$CH_2$—$CH$=$CH_2$ and —$CH_2$—$CH_2$—$CH$=$C(CH_3)_2$.

$R^3$ is hydrogen, alkyl or cycloalkyl of 1 to 10 carbon atoms, eg. methyl, ethyl, propyl, n-butyl, i-butyl, n-pentyl, i-pentyl, n-decyl, cyclopentyl or cyclohexyl, or aryl, eg. phenyl. Examples of suitable starting materials of the formula II are 2-methyl-1,4-diacetoxypent-2-ene, 2,7-dimethyl-1,4-diacetoxyocta-2,7-diene, 2,6-dimethyl-1,4-diacetoxyocta-2,7-diene, 2-ethyl-1,4-diacetoxypent-2-ene, 2-methyl-1,4-diacetoxydec-2-ene and 2-[4-methylpent-3-enyl]-1,4-diacetoxypent-2-ene.

The starting materials of the formula II can be prepared either by brominating the appropriately substituted 1,3-diene and reacting the resulting 1,4-dibromo compound with an alkali metal salt of the appropriate carboxylic acid of the formula $R^3$—COOH, or in a one-stage reaction, by acyloxylating the 1,3-diene with a carboxylic acid and with oxygen in the presence of a catalyst containing, for example, palladium and tellurium (German Pat. No. 2,217,452), platinum and tellurium (German Published Application DAS No. 2,417,558) or palladium and copper (German Published Application DAS No. 2,820,519).

The reaction is carried out in general at from 0° to 200° C., preferably from 80° to 120° C., under atmospheric or superatmospheric pressure, and either batchwise or continuously in the presence of water. The amount of water is advantageously from 1 to 50, in particular from 2 to 20, moles per mole of the starting material of the formula II. Organic solvents which are inert under the reaction conditions may additionally be used. Water-miscible solvents and those having a good dissolving power for water, for example alkanols and cycloalkanols, such as ethanol, methanol, n-butanol, isobutanol, tert.-butanol, glycol, glycerol, sec.-butanol, n-propanol and isopropanol, are particularly suitable for this purpose. It has also proved advantageous to carry out the reaction in the presence of a phase-transfer catalyst, for example a tetraalkylammonium halide.

The reaction is carried out in the presence of an acidic ion exchanger, preferably an acidic synthetic resin exchanger, which is advantageously present in its acid form. Examples of such cation exchangers are all those described in Houben-Weyl, Methoden der Organischen Chemie, volume I/1, page 528, Table 3. Moderately or strongly acidic exchangers, for example those composed of styrene and divinylbenzene and containing sulfonic acid groups, strongly acidic inorganic cation exchangers, such as zeolites, or phenolsulfonic acid resins, polystyrenesulfonic acid resins, styrenephosphonic acid resins or styrenephosphinic acid resins, or appropriate exchangers containing acidic resins, for example those containing bifunctional condensation resins, are preferably used. Examples of suitable acidic resins of the above type are the commercially obtainable products ®Lewatit S 100, ®Amberlit IR-120, ®Lewasorb, ®Dowex 50 WX 8 and ®Amberlyst 15. The amounts of starting materials used, and the amount of exchanger, depend respectively on the selectivity and the number of exchangeable groups in the exchanger used, at the reaction temperature. In general, from 1 to 40 percent by weight, preferably from 5 to 25 percent by weight, based on the starting material of the formula II, of exchanger is used. The amount of water which is present in the dry exchanger and which can be up to 50 percent by weight depending on the structure is not included in the amount of water to be added, as defined above. The form and particle size of the exchanger can be chosen as desired within a substantial range. With respect to the preparation and the use of ion exchangers, reference may be made to the chapter "Ion Exchangers" in the above work.

Instead of an ion exchanger, it is also possible to use a mineral acid, eg. hydrochloric acid, sulfuric acid, nitric acid or hydrobromic acid. From 0.002 to 0.25 equivalent of the stated acid is used per mole of the starting compound of the formula II.

The reaction can, for example, be carried out as follows: a mixture of the starting material of the formula II, water and a mineral acid or the acidic cation exchanger, with or without an organic solvent, is kept at the reaction temperature for from 0.5 to 24 hours. The product of the formula I is then isolated in a conventional manner, for example by filtering off the cation exchanger and fractionally distilling the filtrate. The added mineral acids and small amounts of carboxylic acids, eg. acetic acid, can be removed by neutralization.

The aldehyde of the formula I can be isolated in a particularly simple manner by distilling off and condensing the aldehyde/water mixture in an apparatus for continuously taking off the upper distillate phase of a two-phase mixture. To carry out this procedure, a mixture of the starting compound of the formula II, water and the particular acid or the ion exchanger is heated in a flask to the reaction temperature, and the aldehyde/water mixture which distills off from the reaction mixture is condensed, the condensate separating into an aldehyde phase and a water phase. The water is recycled to the reaction flask, so that the amount of water in the latter remains constant, apart from that consumed in the aldehyde formation. The water consumed can be supplemented during the reaction, if required. Any mineral acid and/or carboxylic acid still present in the crude product can be removed by neutralization, if necessary. The aldehyde is dried with a drying agent, if required, and is then fractionally distilled.

The $\alpha,\beta$-unsaturated aldehydes obtainable by the process of the invention are useful starting materials for the preparation of dyes, crop protection agents and pharmaceutical products. Moreover, they can be used as flavorings in foodstuffs and drinks (German Published Application DAS No. 2,927,090 and DAS No. 2,937,287). 2,7-Dimethylocta-2,6-dienal can, like the isomeric citral, also be used in the preparation of perfumes and cosmetics. Regarding the use of $\alpha,\beta$-unsaturated aldehydes, reference may also be made to Ullmanns Encyclopädie der technischen Chemie, 4th, revised, edition, volume 7, page 118.

In the Examples which follow, parts are by weight.

EXAMPLE 1

The commercially obtainable polystyrenesulfonic acid resin cation exchanger ®Amberlit IR-120 (20–50 mesh, water content 44–48 percent) is used.

A mixture of 22.1 parts of 2-methyl-1,4-diacetoxypent-2-ene, 80 parts of water and 10 parts of the water-containing cation exchanger is heated at 95°–100° C. for 2 hours, and 2-methylpent-2-enal is simultaneously isolated by distilling off and condensing an aldehyde/water mixture in an apparatus for continuously taking off the upper distillate phase of a two-phase mixture. The organic phase is dried with magnesium sulfate and then fractionally distilled. 6.8 parts (63% of theory) of 2-methylpent-2-enal of boiling point 133°–135° C./1,010 mbar, $n_D^{20} = 1.4502$, are obtained.

EXAMPLE 2

A mixture of 11 parts of 2,7-dimethyl-1,4-diacetoxyocta-2,7-diene, 35 parts of water and 4.3 parts by volume of 1N hydrochloric acid (0.1 equivalent of HCl, based on 1 mole of the diacetate) is refluxed for 4 hours. An aldehyde/water mixture is then taken off, as described in Example 1. The resulting organic phase is fractionally distilled, and 4.3 parts (65% of theory) of 2,7-dimethylocta-2,6-dienal of boiling point 80°–82° C./16 mbar, $n_D^{20} = 1.4776$, are obtained.

EXAMPLE 3

The procedure described in Example 2 is followed, and 1.4 parts (58% of theory) of 2,6-dimethylocta-2,7-dienal of boiling point 60°–78° C./16 mbar, $n_D^{20} = 1.4710$, are obtained from 4 parts of 2,6-dimethyl-1,4-diacetoxyocta-2,7-diene, 15 parts of water and 1.6 parts by volume of 1N hydrochloric acid.

COMPARATIVE EXAMPLE 1

The commercially obtainable polystyrenesulfonic acid resin cation exchanger ®Dowex 50 WX 8 (50–100 mesh) is used. The ion exchanger is pretreated with hydrochloric acid and washed neutral with water.

A mixture of 20 parts of 1-methyl-1,4-diacetoxybut-2-ene, 20 parts of water and 5 parts of the cation exchanger is refluxed for two hours. The mixture is cooled to room temperature, the ion exchanger is filtered off, and the organic phase of the two-phase filtrate is separated off in a separating funnel and is dried with sodium sulfate. The resulting 3.5 parts of the organic phase are fractionally distilled, and 2.6 parts (28.9% of theory) of pent-2-enal of boiling point 124°–126° C./1,010 mbar, $n_D^{20} = 1.4359$, are obtained.

COMPARATIVE EXAMPLE 2

A mixture of 100 parts of 2,3-dimethyl-1,4-diacetoxybut-2-ene, 100 parts of water and 27 parts of Dowex 50 WX 8 is refluxed for 2 hours, with stirring. An aldehyde/water mixture is then taken off as described in Example 1. The resulting organic phase (30.4 parts) is fractionally distilled, and 8.5 parts of crude 2,3-dimethylbut-2-enal of boiling point 127°–170° C./1,013 mbar are obtained, corresponding to a yield of crude product of 17% of theory.

We claim:

1. A process for the preparation of an α,β-unsaturated aldehyde of the formula

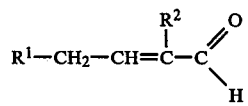

where $R^1$ and $R^2$ are aliphatic hydrocarbon radicals of 1 to 15 carbon atoms, which process comprises reacting a 1,4-diacyloxyalk-2-ene of the formula

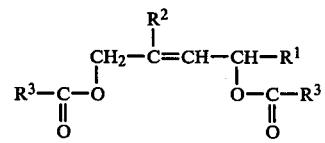

where $R^1$ and $R^2$ have the above meanings and $R^3$ is hydrogen, alkyl, cycloalkyl or aryl, at a temperature of from 0° to 200° C. with water in an amount of 1 to 50 moles per mole of compound II and in the presence of a mineral acid or of a cation exchanger.

2. A process as claimed in claim 1 wherein the reaction is carried out at a temperature of from 80° to 120° C.

3. A process as claimed in claim 1 where the reaction is carried out with from 2 to 20 moles of water per mole of compound II.

4. A process as claimed in claim 3 wherein the reaction is carried out at a temperature of from 80° to 120° C.

5. A process as claimed in claim 1 wherein the reaction is carried out in the presence of from 0.002 to 0.25 equivalent of mineral acid per mole of compound II.

6. A process as claimed in claim 5 wherein the reaction is carried out at a temperature of from 80° to 120° C. and with from 2 to 20 moles of water per mole of compound II.

7. A process as claimed in claim 1 wherein the reaction is carried out in the presence of from 1 to 40 percent by weight of cation exchanger based on compound II.

8. A process as claimed in claim 7 wherein the reaction is carried out at a temperature of from 80° to 120° C. and with from 2 to 20 moles of water per mole of compound II.

9. A process as claimed in claim 8 wherein the amount of cation exchanger is from 5 to 25 percent by weight based on compound II.

* * * * *